United States Patent [19]

Godik

[11] Patent Number: 6,002,958
[45] Date of Patent: Dec. 14, 1999

[54] METHOD AND APPARATUS FOR DIAGNOSTICS OF INTERNAL ORGANS

[75] Inventor: Eduard E. Godik, Washington Township, N.J.

[73] Assignee: Dynamics Imaging, Inc., Mahwah, N.J.

[21] Appl. No.: 08/491,865

[22] PCT Filed: Dec. 1, 1993

[86] PCT No.: PCT/US93/11655

§ 371 Date: Jun. 15, 1996

§ 102(e) Date: Jun. 15, 1996

[87] PCT Pub. No.: WO94/28795

PCT Pub. Date: Dec. 22, 1994

[30] Foreign Application Priority Data

Dec. 24, 1992 [RU] Russian Federation .......... 92 014 137

[51] Int. Cl.⁶ ............................................. A61B 5/05
[52] U.S. Cl. .................. 600/407; 600/473; 600/437; 250/339.11
[58] Field of Search .................. 128/653.1, 664, 128/665, 633, 660.01, 661.07, 660.04, 661.04; 250/330, 339, 341, 339.01, 339.11, 341.1, 341.8; 600/407, 473, 426, 310, 437, 453, 440, 450; 73/657

[56] References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,207,901 | 6/1980 | Nigam | 128/660 |
| 4,212,306 | 7/1980 | Mahumud | 128/660 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |
| 4,339,954 | 7/1982 | Anson et al. | 600/476 |
| 4,385,634 | 5/1983 | Bowen | 128/653 |
| 4,434,799 | 3/1984 | Taenzer | 128/660 |
| 4,495,949 | 1/1985 | Stoller | 128/664 |
| 4,515,165 | 5/1985 | Carroll | 128/664 |
| 4,536,790 | 8/1985 | Kruger et al. | 358/111 |
| 4,570,638 | 2/1986 | Stoddart et al. | 128/665 |
| 4,573,472 | 3/1986 | Ito | 128/399 |

(List continued on next page.)

FOREIGN PATENT DOCUMENTS

| | | |
|---|---|---|
| 0099756 | 2/1984 | European Pat. Off. . |
| 0108617 | 5/1984 | European Pat. Off. . |
| 0140633 | 5/1985 | European Pat. Off. . |
| 0447708A3 | 9/1991 | European Pat. Off. . |
| WO79/00594 | 8/1979 | WIPO . |
| WO 89/00278 | 1/1989 | WIPO . |
| WO 91/06244 | 5/1991 | WIPO . |

OTHER PUBLICATIONS

Godik, E.E., Guljaev, Yu.V., "The Human Being Through 'Eyes of Radiophysics'", Journal of Radio Engineering (Russian) 1991, No. 8, pp. 51–62.

Ring, E.F.J. and Hughes, H. "Real Time Video Thermography", in Recent Developments in Medical and Physiological Imaging a supplement to Journal of Medical Engineering and Technology, 1986, pp. 86–89.jf124c Primary Examiner—Brian L. Casler
Attorney, Agent, or Firm—Jerry Cohen; Jacob N. Erlich

[57] ABSTRACT

The invention relates to medicine, or exactly to methods of non-invasive investigations of a living organism state, in particular, for diagnostics of pathological changes in tissues of human and animals organism. The apparatus relies upon illuminating the investigated organ of the body with infrared radiation of 0.6–1.5 um wavelength range and simultaneous scanning of the investigated organ volume with a focal spot of a focused beam of amplitude-modulated ultrasound waves, at least one of the parameters which appear as a result of the transmitted and/or back scattered infrared radiation being recorded. The presence and the type of pathology in the investigated organ is judged by the value and/or the characteristics of the relative changes in the above mentioned parameters during the scanning process.

26 Claims, 4 Drawing Sheets

U.S. PATENT DOCUMENTS

| | | | |
|---|---|---|---|
| 4,576,173 | 3/1986 | Parker et al. | 128/633 |
| 4,583,869 | 4/1986 | Chive et al. | 374/122 |
| 4,649,275 | 3/1987 | Nelson et al. | 250/358.1 |
| 4,767,928 | 8/1988 | Nelson et al. | 250/341 |
| 4,774,961 | 10/1988 | Carr | 128/736 |
| 4,798,209 | 1/1989 | Klingenbeck et al. | 128/653 |
| 4,807,637 | 2/1989 | Bjorkholm | 128/664 |
| 4,810,875 | 3/1989 | Wyatt | 250/227 |
| 4,817,038 | 3/1989 | Knoll et al. | 364/413.24 |
| 4,817,622 | 4/1989 | Pennypacker et al. | 128/664 |
| 4,829,184 | 5/1989 | Nelson et al. | 250/358.1 |
| 4,834,111 | 5/1989 | Khanna et al. | 356/351 |
| 4,862,894 | 9/1989 | Fujii | 128/666 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,007,428 | 4/1991 | Watmough | 600/473 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,174,298 | 12/1992 | Dolfi et al. | 600/476 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 600/473 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Valdes Sosa et al. | 128/653.1 |
| 5,309,907 | 5/1994 | Fang et al. | 128/633 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,371,368 | 12/1994 | Alfano et al. | 250/341.1 |
| 5,515,847 | 5/1996 | Braig et al. | 128/633 |
| 5,572,996 | 11/1996 | Doiron et al. | 128/633 |

OTHER PUBLICATIONS

Platonov, S.A., . . . , Godik, E.E., "Informative Tasks of Functional Mapping of Biological Subjects", *Journal of Radio Engineering* (Russian) 1991, No. 8, pp. 62–68.

Jacquez, J.A. et al, "Spectral Reflectance of Human Skin in the Region 235—1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

Krenkel, T.E., Kogan, A.G. and Tatatorian, A.M., "Personal Computers in Engineering", Izd. Mir, RiS, (Russian) 1989, p. 71.—copy not available.

Dgagupov, R.G. and Erofeev, A.A., *Piezo–Ceramic Elements in Instrument Designing and Automatics*, Leningrad, Izd. Mashinosroenie, 1986, pp. 154–155 (Russian).—copy not available.

Svechnikov S.V. "Optoelectronics elements", Moscow, Izd, "Sov. Radio" 1971, pp. 250–256.—copy not available.

Legett, Kate, *Optical mamography offers promise as alternative to x–ray detection*, Biophotonics International, Jan./Feb., 1996, pp. 56–57. This publication has been submitted as representative of a recent development in the field of mamography.

Godik, Eduard E. and Gulyaev, Uri, V., "Functional Imaging of the Human Body," *IEEE Engineering in Medicine and Biology*, Dec. 1991, pp. 21–29.

*Physics of image visualization in medicine*, C. Webb, ed., vol. 2, p. 382, Moscow, Mir, 1991 (Translated from English) (copy not available).

*The comparison of the sensitivity of ultrasound echo and shadow methods for determination of calcification of breast tissues*, Proc. Conf, Ultrasound Biology & Mecicine—Ubiomed. VI, Warsaw–Jablonna, Sep. 19–23, 1983, pp. 41–49 (copy not available).

Ichimury, A. *Wave propagation and scattering in randomly inhomogeneous media*, vol. 1, pp. 74–79, Moscow, Mir, 1981 (Translated from English) (copy not available).

Barabanenkov, Yu. N. *On the relative increase in radiation extinction length due to correlation of weak scatterers*, USSR Academy of Sci Proceedings, Physics of atmosphere and ocean, vol. 18, No. 7, pp. 720–726, 1982 (copy not available).

Vartapetjan, M.A. et al. *Sensor perception, An investigation experience with the help of focused ultrasound*, Leningrad, Nauka, 1985 (Russian).

*Biophysical approach to the problem of safety under the ultrasound diagnostics*, Proc. Conf. Ultrasound Biology & Medicine—Ubiomed. YI, Warsaw—Jablonna, Sep. 19–23, pp. 95–99, 1983 (copy not available).

Titce, U. and Shenck, K. *Semiconductor scheme technology*, p. 144, Moscow, Mir, 1982 (Translated from English to Russian) (copy not available).

Krenkel, T.E. et al. *Personal computers in engineering practices*, pp. 71–75, Moscow, RiS, 1989 (Russian) (copy not available).

Guljaev, Yu.V., Godik, E.E. et al. *On the possibilities of the functional diagnostics of the biological subjects via their temporal dynamics of the infrared images*, USSR Academy Nauk Proceedings/Biophysics—1984, vol. 277, pp. 1486–1491 (copy not available).

Hasset, J. *Introduction into psycho–physiology*,—Moscow, Mir. 1981 (Translated into Russian) (copy not available).

Godik, E.E., Guljaev, Yu.V. *Human and animal physical fields*, V mire nauki (Russian version of Scientific American) /1990, No. 5, pp. 74–83 (copy not available).

de Haller EB and Depeursinge C. Simulation of time–resolved breast transillumination. *Medical & Biological Engeering & Computing* 1993; 31:165–70.

Gandjbakche AH, Nossal R, and Bonner RF. Resolution limits for optical transillumination of abnormalities deeply embedded in tissues. *Medical Physics* 1994; 21:185–91.

Hebden JC and Kruger, RA. Transillumination imaging performance: A time–of–flight imaging system. *Medical Physics* 1990; 17:351–6.

Levin DC, Schapiro RM, Boxt LM, Dunham L, Harrington DP, and Ergun DL. Digital subtraction angiography: principles and pitfalls of image improvement techniques. AJR 1984; 143:447–454.

Sabel M, Horst A. Recent developments in breast imaging (Review). *Physics in Medicine and Biology* 1996; 41:315–68.

Sickles EA. Breast CT scanning, heavy–ion mammography, NMR imaging, and diaphanography. In Feig SA and McLelland R eds. *Breast Carcinoma: Current Diagnosis and Treatment* 1983; New York: Masson, 233–50.

Marks, Fay A. et al, A comprehensive approach to breast cancer detection using light; photon localization by ultrasound modulation and tissue characterization by spectral discrimination, SPIE vol. 1888, pub. Sep. 1993, pp. 500–510.

METHOD AND APPARATUS FOR DIAGNOSTICS OF INTERNAL ORGANS

CROSS REFERENCE TO RELATED APPLICATIONS

This application claims priority of Applicant's prior PCT Application Ser. No. PCT/US93/11655 having an International Filing Date of Dec. 1, 1993 and Russian Application Ser. No. 92014137 having a filing date of Dec. 24, 1992.

BACKGROUND OF THE INVENTION

The invention relates generally to medicine, or more particularly to methods of non-invasive investigations of living organisms, and more specifically, for diagnostics of pathological changes in tissues of human and animal organisms.

A number of methods of medical diagnostics, which employs transillumination of organs and tissues by radiation, are known. One of the most widely used is X-ray diagnostics (see Physics of image visualization in medicine. C. Webb, ed., vol. 2, p. 382, Moscow, Mir, 1991 (Translated from English)) but this method is not safe for a patient and the serving personnel, since sources of ionizing radiation are used during the corresponding procedure.

The above mentioned disadvantage is not applicable to ultrasound diagnostics (see U.S. Pat. No. 4,434,799 cl. A 61 B 10/00, NKI 128 660, 1984) which is a non-invasive method, practically harmless both to patients and personnel. It permits revealing sufficiently small pathological growths (about 3 mm diameter) (see The comparison of the sensitivity of ultrasound echo and shadow methods for determination of calcification of breast tissues/ Proc. Conf. Ultrasound Biology & Medicine—Ubiomed. YI, Warsawjablonna, Sep. 19–23, 1983, pp. 41–49). However, this method is sensitive only to the acoustic "contrast" of pathological tissue, which is often insufficient to identify the type of the pathology.

Good possibilities for identifying the type of the pathological tissues may be possible by optical spectroscopy. The method closest to the present is a spectral method of optical diagnostics of internal organs, based on transillumination of the investigated organ by radiation of the near infrared (NIR), 0.6–1.5 um wavelength range and recording of the intensity of the transmitted illumination at several wavelengths. The presence of a "shadow" or a change in the photodetector output signal serves as a criterion of the pathology. This method may be considered similar to the present method and equipment.

This method, has however, considerable disadvantages over the present invention: strong scattering of optical radiation in tissues, provoked by their micro-inhomogeneity, does not permit revealing a pathology growth in the investigated organ depth, if the growth size is much less than the distance separating it from the organ front and bottom surfaces.

The known apparatus for the realization of the transillumination method (see U.S. Pat. No. 4,807,637, cl. A 61 B 6/08, NKI 128–664, 1989) contains an NIR-radiation source with an optical system and a photodetecting device, coupled to a recorder. The investigated organ, a mammary gland, for example, is placed between two transparent plates, compressing the organ and shaping it into a plane-parallel, trapezoid or other forms. The means of moving the "NIR-radiation source—photodetecting device" pair over the organ surface are also available. The main disadvantage of this apparatus is its low sensitivity in revealing the pathology at an early stage due to the above mentioned strong scattering of NIR-radiation by biological tissues.

The task of the invention is elimination of the above mentioned disadvantages of the prototype, i.e. to achieve increasing in the spatial resolution under the conditions of a strong optical NIR-radiation scattering by the investigated tissues.

SUMMARY OF THE INVENTION

The invention is directed to the method and apparatus of optical diagnostics of human body internal organs, based on the illumination of the investigated organ with near IR (NIR)-radiation of 0.6–1.5 um wavelength range and recording of the transmitted and/or back scattered radiation parameters at several discrete wavelengths, an additional focused beam of amplitude-modulated ultrasound waves, the focal spot of this beam scanning the volume of the body investigated and, simultaneously with, at least one of the parameters of modulation of the intensity of the transmitted and/or of back scattered radiation of the infrared radiation, appearing under these conditions, being recorded. The presence and the type of pathology being judged by the value and/or the character of the relative change in the above mentioned parameters of modulation during the scanning process.

A pulse modulation of the intensity of the ultrasound waves beam is employed, and the amplitude of modulation of the infrared radiation appearing under these conditions is recorded.

During the diagnostic process, the duration and the duty cycle of the pulses of the modulation intensity of the ultrasound waves beam are varied, and at least one of the parameters of the transient process of the intensity modulation of the scattered infrared radiation is recorded.

An apparatus for realization of the method includes a transparent support base both for NIR radiation and ultrasound for a body investigated, illuminators and detectors of the radiation placed from the both sides of the support, a scanning system, a block for signal processing and control, a reflecting device and an oscillator of ultrasound focused waves with an electrical generator, a modulator, illuminators and photodetectors control blocks, an amplifier and a synchronous integrator, the ultrasound focusing oscillator being coupled to the scanning system in the plane of the transparent support and connected with the generator and the modulator. Manageable spectrally-selective photodetectors are connected with the block of signal processing and control via the sequentially connected photodetectors control block, amplifier and synchronous integrator; the modulator output is connected with the synchronizing input of the synchronous integrator, and the illuminators inputs are connected with the corresponding control block outputs, the synchronizing inputs of the illuminators and photodetectors control blocks being connected with the outputs of the signal processing and control block.

The apparatus support is in the form of plates, transparent both for infrared and ultrasound radiation. The photodetectors can be placed inside the plates body and turned to present their sensitive surfaces to each other. Besides, radiating elements of the photodetectors and the illuminators can be placed inside the body of at least one plate. The ultrasound focusing ocsillator is placed at a camera, filled with an immersion medium and covered by the (transparent both for NIR and ultrasound) support or base plate, the oscillator acoustic axis crossing the plate plane.

The oscillator can be in the form of a piezo-electric transformer with the electrodes divided into sections and connected via manageable phase rotators to the generator, the control inputs of the latter being connected with the signal processing and control block.

DETAILED DESCRIPTION OF THE PREFERRED EMBODIMENT

The present invention is based upon the fact, established by the inventor for the first time, that the spatial resolution of the optical transillumination method can be considerably increased by the application of ultrasound waves under the conditions of strong optical inhomogeneity of the subject investigated. As mentioned above, optical inhomogeneity of the investigated subject results in an abrupt deterioration of the metrological characteristics of the transillumination method, since the "shadow" recorded can exceed considerably the size of a pathological growth and this is connected in a rather complex way with the pathology location in the strongly scattering medium.

The use of an ultrasound beam makes it possible to realize a new approach to revealing pathological growths. The effect of the intensity modulation of optical radiation, transmitted through or/and back scattered by biological tissue, is connected to periodical changes in the tissue density under the influence of deformation (pressure), periodically switched on and off at the focus of the amplitude modulated ultrasound beam. Biological tissues are known to change their transparency under the application of pressure (see Ichimury, A. Wave propagation and scattering in randomly inhomogeneous media, vol. 1, pp. 74–79, Moscow, Mir, 1981 (Translated from English)) as a result of changes in the real and imaginary parts of the medium dielectric permeability. The real part (the refraction coefficient) is changed practically non-inertially under pressure application, due to "condensing" of scatterers (see Barabanenkov, Yu. N. On the relative increase in radiation extinction length due to correlation of weak scatterers/USSR Academy of Sci. Proceedings, Physics of atmosphere and ocean, vol. 18, No. 7, pp. 720–726, 1982) and changes in the imaginary part (the absorption coefficient, mainly by blood) take place with a delay of several seconds, as a result of blood expelling from the capillaries (vessels). This effect represents some kind of the acoustic optical palpation, making up the basis for revealing the pathology via the contrast in compression, the latter being transformed into the amplitude modulation contrast of the transmitted or/and back scattered optical beam.

Another sensory (but not the tissue) mechanism of the "acoustic optical palpation" is possible to be realized at much less ultrasound beam densities. In the latter, a modulated ultrasound beam irritates the biological tissue receptors (blood vessels cell walls, for the first time). It could be mechanical receptors, thermal receptors and non-specific nerve outer sheaths. As a result, capillary blood flow at the effected zones is modulated, for example, at the skin areas related to the internal organs—Zakharjina-Ged zones. This produces the corresponding modulation of the optical transparency of the tissue investigated. The latter effect is more inertial (from several seconds to minutes), but the necessary intensities of the ultrasound waves are very small and are determined by the reception threshold. The contrast, in order to reveal a pathological growth in this case, is formed as a result of the differences in the sensitivity thresholds for normal and pathological tissues to the influence of the modulated ultrasound beam. Both effects of the "acoustic optical palpation"—via direct modulation of tissue optical parameters and the sensory ones—could be used in cooperation for pathology revealing and identification.

In particular, the changes in the modulation amplitude and/or the parameters, characterizing the transient process at the beginning or/and the end of the ultrasound beam influence, the scattered optical radiation (transmitted through or back scattered by the tissue investigated) at the pathology area as compared with normal tissues, i.e. the "contrast" value, serve as an indicator of pathology. Or, in the other words, a focused ultrasound beam performs the function of the probe. The use of such a probe permits not only the revelation of the pathology, but also its identification by means of recording the dependence of the modulation amplitude and/or the transient parameters on the wavelength of NIR-radiation, as well as on the parameters of the ultrasound waves modulation: the frequency and power of the ultrasound beam, the duration of the influencing pulses and their duty cycle etc. All of the above opens up the possibility of performing a non-invasive spectral analysis of a suspected pathological area inside the depth of the investigated organism, for example in the mammary gland, in the liver etc.

Ultrasound probes (US-probes), i.e. the sources of ultrasound waves, representing ultrasound focusing transformers supplied with the scanning means, are known in biology and medicine (see Vartapetjan M. A. et al. Sensor perception. An investigation experience with the help of focused ultrasound, Leningrad, Nauka, 1985 (Russian)). Their main object is to provoke local changes in the tissue features from point to point over the scanning direction and to compare the features of the nearby sites. Biological influence of the focused ultrasound waves is caused by the combined action of a number of factors (mechanical, thermal etc.), that could be recorded both via changes in the acoustic characteristics (see Patent application of Great Britain No. 1403241, cl. GO1N 29/04, NKI H4D, 1975), and changes in electrical tissue conductivity (see USSR Patents No. 1533648, cl. A61B 5/02, 1986 and No. 1641268, cl. A61B 5/0295, 1986). In the latter case, ultrasound waves are modulated and the electric signal received is separated by a synchronous detection at the ultrasound frequency modulation.

The preferred embodiment of the ultrasound (US) probe is chosen on the basis of the following considerations:

The density of the ultrasound waves at the focal spot area is to be set up not higher than 1 $kW/m^2$ of continuous ultrasound radiation, since such "diagnostic" ultrasound waves at the range of frequencies of 0.3–10 MHz and the exposition times from 1 s up to 500 s are known not to be accompanied by any irreversible effects (see Biophysical approach to the problem of safety under the ultrasound diagnostics/Proc. Conf. Ultrasound Biology & Medicine—Ubiomed. YI, Warsaw Jablonna, Sep. 19–23, pp. 95–99, 1983). In addition, the work should be performed under the pain threshold of sensitivity, the latter, being dependent on the type of organ investigated, can aggravate the above mentioned restrictions (see Vartapetjan M. A. et al. Ibid.)

The frequency of the ultrasound waves is to be chosen to be in the range of 0.3–10 MHz. In this case, the diameter of the focal spot in the investigated tissue would be between one millimeter and one tenth of a millimeter, depending on the modulation frequency.

A pulse modulation of the ultrasound beam is used. The frequency of the pulses is usually chosen to be in the range from about one tenth of a hertz to tens of kilohertz. When the ultrasound beam is variably modulated, the amplitude of the first harmonic of the scattered infrared radiation modulation, appearing under these conditions, is synchronously recorded. When the US-beam is pulse modulated with the intervals between pulses exceeding the time constant of the recovery of the tissue's optical characteristics after the deformation provoked by the influence of the US-beam, then not only is the amplitude of the modulation of the scattered NIR-radiation measured, but also the form of the pulses of this radiation is recorded with the help of a strobe-integrator. In addition, the parameters of the transient processes are measured following the US-beam switching on and off, including time delay between the beginning of changes in the intensity of NIR-radiation in answer to these switchings. The following parameters of the pulse modulation are chosen: the pulse duration of the ultrasound waves, from tens of seconds to milliseconds; sequence frequency, from tenths of hertz to tens of kilohertz. The optimal pulse durations and intervals between them are selected for different tissues during special experiments.

Figure 1:
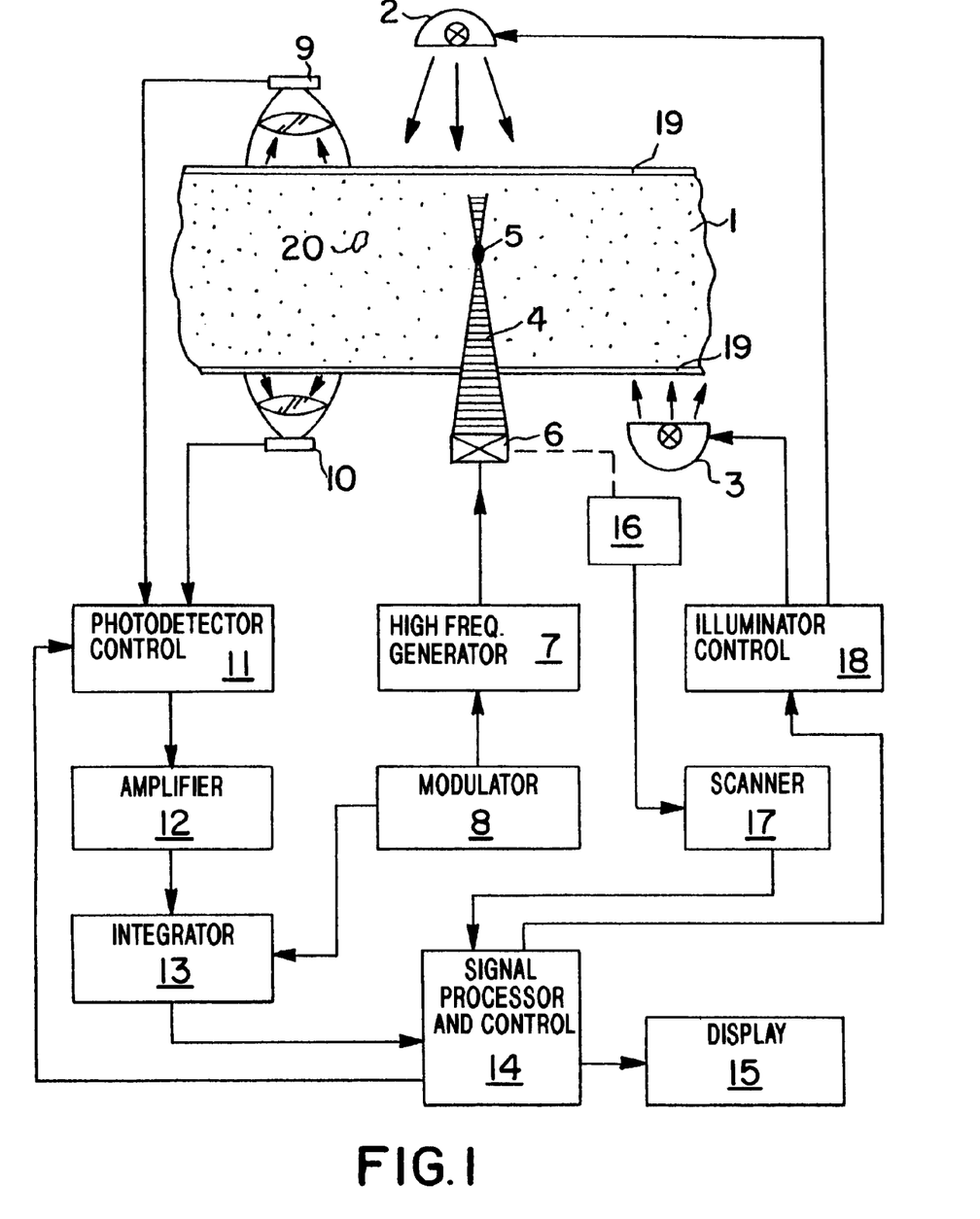
FIG. 1 is a schematic block diagram of the apparatus of this invention.

The method of the present invention can be realized with the help of the apparatus shown in FIG. 1. A body under investigation (or its organ) 1 is illuminated from illuminators 2 and 3 by NIR-radiation beams, each of the beam widths being unlimited and could be of the same magnitude as the size of the organ investigated. Simultaneously, investigated body 1 is scanned by focused beam 4 with focal spot 5 from ultrasound oscillator 6. Oscillator 6 is coupled to a high frequency generator 7 of continuous electrical oscillations, the modulation of the latter being performed with modulator 8. The transmitted and back scattered NIR-radiation is recorded with help of photodetectors 9,10, supplied with a lens and a reflector, receiving the scattered light, which is coupled via photodetector 11 control block to amplifier 12. The signal from the output of amplifier 12 is received by synchronous integrator 13, and then by block 14 of the signal processing and control. A synchronizing signal is received by block 13 from modulator 8. When variable modulation of the US-beam is performed, a synchronous detector is usually used as the integrator 13. Under the conditions of the modulation with pulses of a sufficiently small duty cycle, a strobe-integrator with an electric control is used (see Titce, U. and Shenck, K. Semiconductor scheme technology, p. 144, Moscow, Mir, 1982 (Translated from English to Russian)). Block 14 can be in an analog or a digital form; in the latter case, a personal computer is sufficient for performing the apparatus control via the input-output controller, as well as for -the data processing and their display on a monitor. Information from block 14 of the signal processing and control is received by display 15. Ultrasound oscillator 6 is supplied with scanner driver 16, connected with block 17 of US-probe scanner. Scanner block 17 output is connected with input of block 14 of signal processing and control. The intensity and the spectral composition of NIR-radiation is set up with the help of illuminator control block 18.

The operation of the invention takes place as follows. Investigated body 1, or a part of it, is placed on support elements 19. Simultaneously with illumination of investigated body 1 with the help of the NIR radiation source, the scanning of the area investigated by a focused beam 4 of the ultrasound waves is performed. Focal spot 5 is moved up and down, as well as from right to left, in accordance with a scanning regime, provided by blocks 14 and 17, and at each point scanned, the modulated scattered NIR-radiation (transmitted or back scattered) is received and recorded by photodetectors 9 and 10. To increase the intensity of the light received, light gathering lenses are placed before the photodetector's sensitive plates and a reflector behind them.

Figure 2:
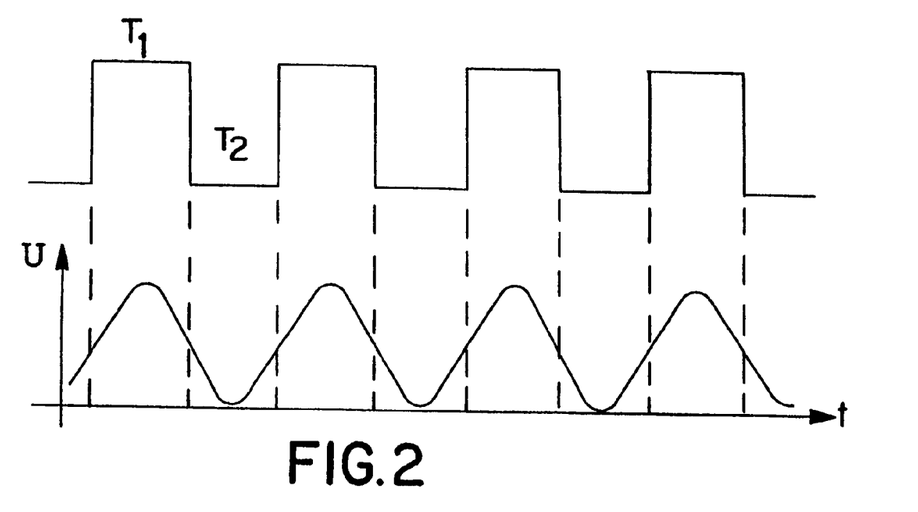
FIG. 2 is a graphic representation of the varying modulation of the ultrasound probe utilized with the invention.
Figure 3:
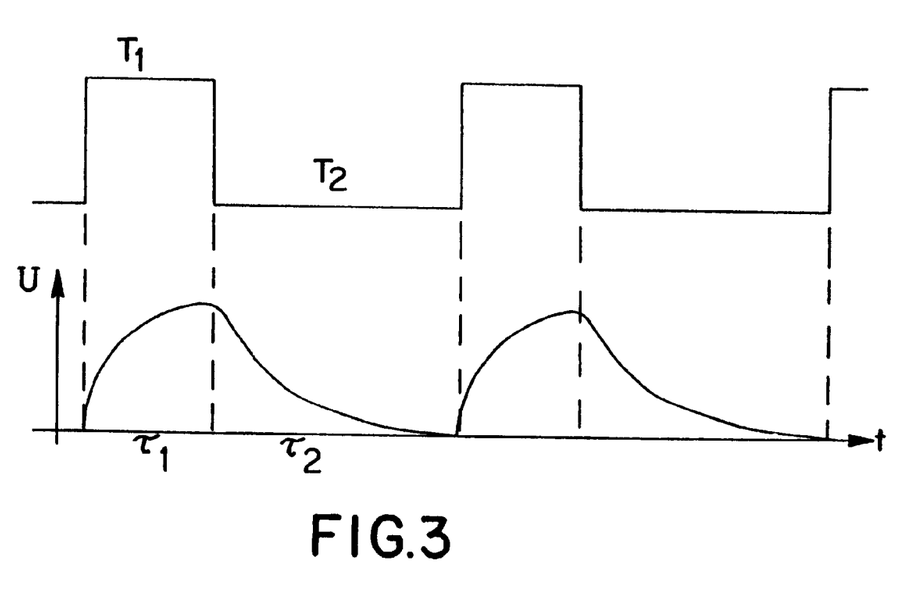
FIG. 3 is a graphic representation of the IR signals utilized with this invention.

When the variable modulation of the US-beam is applied, the form of the evoked modulation of the scattered NIR-radiation is close to the sinusoidal wave shown in FIG. 2: the upper curve shows the form of the US-beam modulation, and the lower one that of the NIR-radiation). It is convenient to also use a pulse modulation with the pulse duration larger than the recovery time of the investigated tissue optical characteristics. In this case, not only the amplitude of the modulation of the scattered NIR radiation, provoked by the ultrasound deformation, but also the transient processes parameters—a delay in the beginning of the changes in the NIR-radiation intensity after switching on and off the ultrasound waves, the time constant of these processes, the position at the time axis and the extrema amplitudes etc.—are recorded. Under these conditions, the form of the modulation pulses of the scattered NIR-radiation is recorded synchronously with the help of the strobe-integrator (see FIG. 3, the disposition of the curves are the same as in FIG. 2). To realize the influence of the modulated ultrasound beam on the given area, instead of special modulator 8, a periodical shifting of a normal, non-modulated US-beam from one part of the body investigated to the other one is performed with the help of scanning block 17, the latter being managed by control block 14, according to the assigned program.

At the absence of any pathology, the input signal will be characterized by some value of the modulation, typical of normal tissues. If focal spot 5 falls into the zone of a pathological growth 20 and becomes coincident with it, at least one of the parameters of the NIR-modulation, received by photodetectors 9 and 10 (by both or by one of them), will change, indicating the presence of the tissue inhomogeneity and of possible pathology. It is a combined recording of the output signal and the changes in the position of focal spot 5 (via information from scanning block 17) over the investigated area that gives the possibility to localize the pathological growth and to draw the growth contour, or in other words, to perform mapping.

To identify the type of the pathology, the focal spot 5 is fixed at the pathological growth and spectral dependencies of the amplitude of the output signal are recorded, while varying the spectral composition of the illuminating radiation and/or of the optical radiation recorded. In addition, the dependence of the parameters of the NIR-radiation modulation on the parameters of the US-beam modulation (pulse duration, the duty cycles, power, the ultrasound waves carrying frequency) are recorded with the-same aim.

The device for realization of the method of this invention in the part that relates to the supplementing the apparatus with the means of the ultrasound beam forming and scanning or the arrangement of US-probe, can be accomplished with the use of the elements adopted to the ultrasound diagnostics, see Vartapetjan M. A., et al. Ibid., for example.

Figure 4:
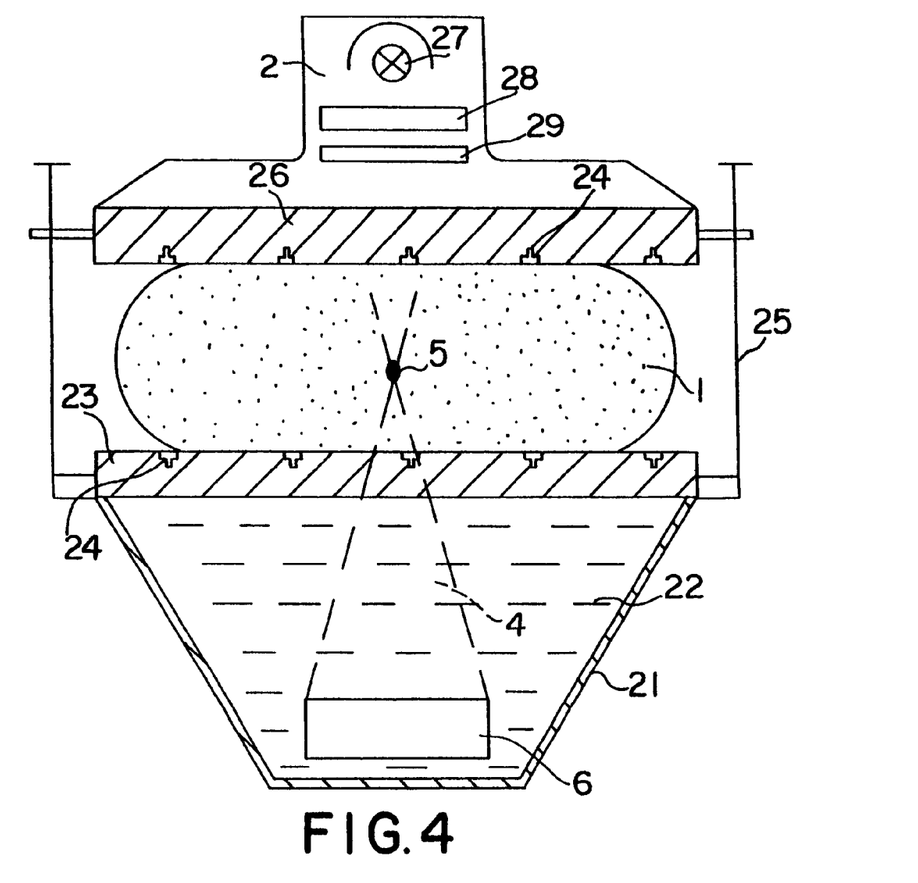
FIG. 4 is a schematic, cross-sectional representation showing the ultrasound oscillator and illuminator utilized with this invention.

The device shown in FIG. 4 represents a hermetic frame 21 filled with an immersion medium 22, of water free of gases, for example. Ultrasound oscillator 6 connected with the scanning facilities (not shown) is placed at the cavity. Oscillator 6 with the facilities for forming focal spot 5 can be in the form of an electro-acoustical piezo-transformer, supplied with an acoustical lens. If the latter is omitted, a sectioned piezo-transformer is used, each section being connected via a manageable phase-rotor with the generator of the electrical oscillations (see U.S. Pat. No. 4,207,901, cl. A 61 B 5/00, NKI 128–660, 1980). In the latter case, controlled moving of the focal spot 5 can be performed both in the axial and in the transverse directions without use of any mechanical scanning mechanisms.

Frame 21 is optically (and acoustically) closed at the front surface with transparent cover/support 23 made from an organic glass, for example, or from other transparent plastic material. Such plastic protectors are widely used in the ultrasound technology, since they are characterized by relatively low decay of ultrasound waves at the frequency of up to 10 MHz. Photodetectors 9, 10 are placed in cover/support 23 and are in the form of one or several photo-sensitive elements 24, having their sensitive parts adjacent to the outer surface of cover/support 23. They could be arranged in a random manner, however, a uniform distribution over the cover/support area is mostly used.

In the case, when a sectioned piezotransformer (see U.S. Pat. No. 4,207,901) is used, a local bath with the immersion medium, together with cover/support 23, can be shaped in the form of a solid state sound guide.

Illuminating device 2 capable of moving up and down is fixed to the other side of cover/support 23 which is in the form of optically transparent plate 26, supplied with an illumination source, an incandescent lamp or light diodes, for example, and is moveable with respect to cover/support 23.

In one example, to provide a wide illuminating beam, lamp 27 is supplied with an optical system which is in the form of condenser 28 and changeable filters 29, setting up the necessary radiation spectral range.-Instead of filters, a monochromator of any type can be used. The monochromator or filter's operation is controlled by illuminator control 18. Inside the body of plate 26, the photodetectors are installed, the sensitive elements 24 of the latter being oriented towards the photodetectors placed at the surface of cover/support 23. The photodetectors, placed both at cover/support 23 and at plate 26, are coupled to the control block 11, the latter possessing several inputs, each for each photodetector. Block 11 provides the necessary spectral range of the received radiation with the help of known means: monochromators or changeable filters.

Figure 5:
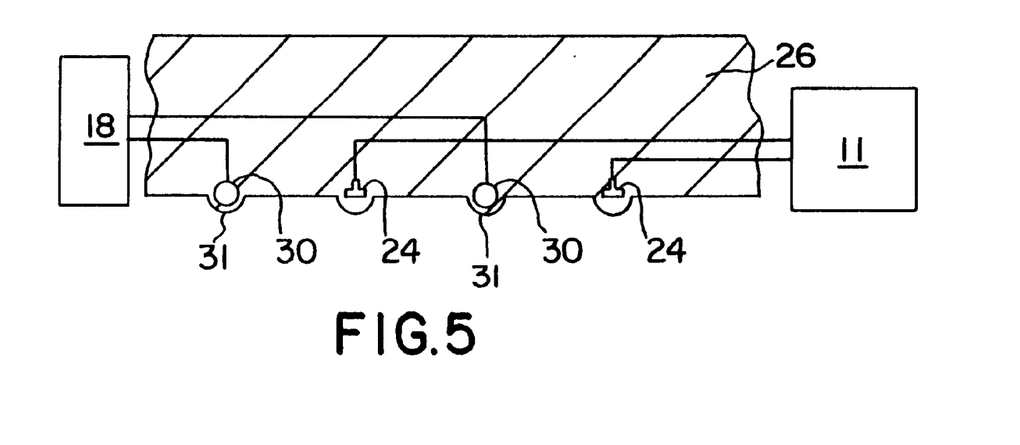
FIG. 5 is a schematic, cross-sectional view of the photodetectors and light -emitting diodes arrayed in one of the plates used in this invention.

In another example, when light diodes 30 are used as the NIR-radiation sources, they are disposed in such a manner as shown in FIG. 5 that both sensitive elements 24 of the photodetectors and light diodes 30 are located at the same side of plate 26. The base of plate 26 is made to be non-transparent for the NIR-radiation, in order to exclude direct illuminating of sensitive elements 24 by light diodes 30, since a working point of the photodetectors can be shifted due to such illumination. A configuration could be given to the working surface of plate 26, so that elements 31 could be properly inserted into it and are capable of correcting the diagram of the radiation directionality. As such elements, lens and photons could be used. The above configuration of the light radiating and the radiation receiving surfaces of plate 26 makes it possible to provide sufficiently good light contact of the illuminator with the patient body. To perform the spectral analysis of the pathological inhomogeneity, light diodes 30 are divided into groups with different wavelength of radiation, which are switched on alternatively one after another from each group. These groups are connected with illuminator control block 18, providing a choice of the corresponding light diodes groups.

Plate 26 in the apparatus, working both with the transmitted and reflected (back scattered) light, is moveble into frame 21 so that the investigated organ could be formed into a flat, smooth condition. Conventional springs could serve as the means of such movement, as well as pneumatic drivers with a progressive movement, or other known devices of a similar assignment with a smooth action.

Figure 6:
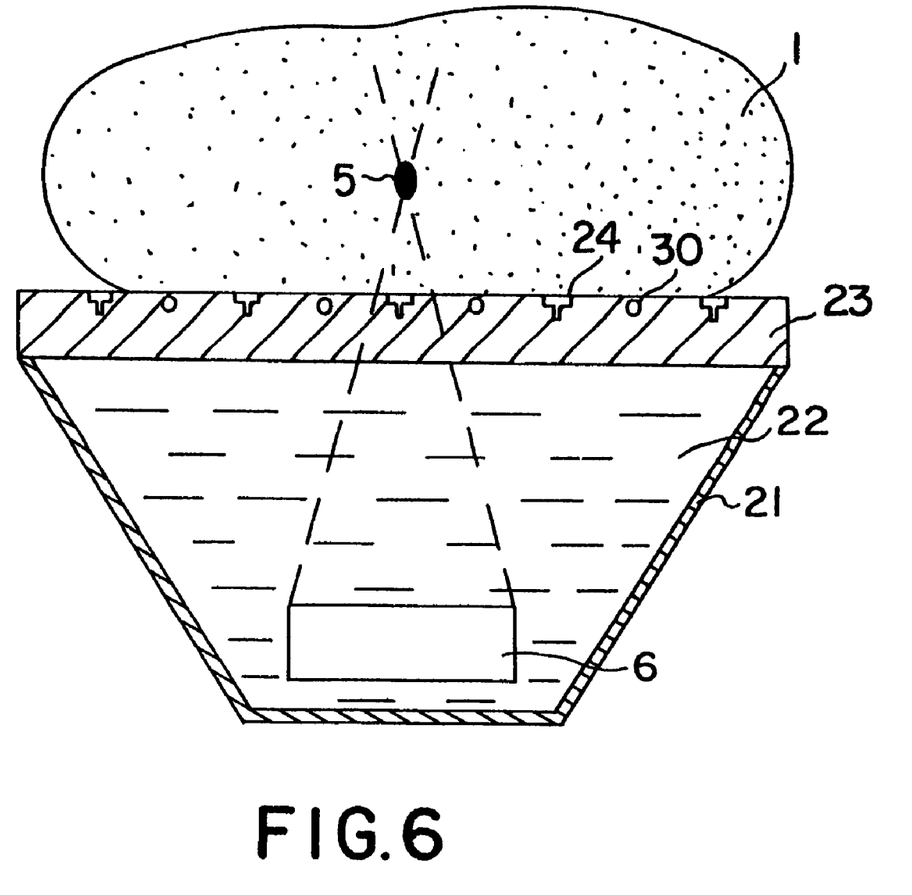
FIG. 6 is another embodiment of this invention illustrating in a schematic, cross-sectional view the ultrasound oscillator and photodetector devices when an object under investigation is viewed from one side only this invention.

For the case when the anatomic peculiarities or the physical state of a patient do not permit carrying out the investigation in the transmitted light, the apparatus of the invention may be modified for the investigation of an organ, such as the liver for example, which is accessible from one side. As shown in FIG. 6, in this latter case, the NIR-radiation sources—light diodes 30 and sensitive elements 24 of the photodetectors are arranged directly in the cover/support 23 and their disposition can be random or uniform, as in the case, shown in FIG. 5.

The method utilizing the apparatus of this invention is described in the following manner. The investigated organ 1, a mammary gland, for example, is placed at the surface of cover/support 23 while plate 26 is moved upward. Then plate 26 is moved down under the action of springs or pneumatic driver until the investigated organ forms into a flat and smooth form. The system of the IR radiation illumination (lamp 27 or light diodes 30) is switched on and the corresponding radiation spectrum is set up, that for lamp 27 with the help of filters 29 and that for photodiodes 30 by switching on of the corresponding group at illuminator control block 18. Ultrasound oscillator 6 and driver 16 of the scan system of the US-probe are then switched on. In the case, when during the operation of the apparatus, focal spot 5 of the US-probe coincides with pathological growth, at least one of the parameters of the modulation of the optical signal recorded by the photodetectors must change. Simultaneously, signals representative of the US-probe coordinates are received by block 14 from scanning block 17 which permits the construction of a map of the dependency of the amplitude of optical radiation modulation on the investigated point coordinate. At such a map, the areas differing (by contrast) from the surrounding tissues can be revealed. The set of these data, i.e. the spectral dependence of at least one of the parameters of the modulation of the scattered NIR-radiation, the dependency of the latter on the parameters of the ultrasound beam modulation, as well as on the ultrasound carrying frequency at fixed NIR-radiation wavelengths, makes it possible to identify the type of the pathology by comparing this data set with similar characteristics for different pathological tissues.

The apparatus realization can be performed both with the help of an analog means and digital technology. In particular, the signal processing block 14 and the display 15 can be realized on the basis of a computer (see Krenkel, T. E., et al. Personal Computers in Engineering Practice, pp.71–75, Moscow, RiS, 1989). The illuminator control 18 adjusts, after the computer command, the necessary level of the illumination intensity, as well as the spectral composition either for one common radiation source or for each of the separate sources. The principles and the means of such constructions are well known in the technology and are not the subject of the invention. In a similar way, also from the computer, the wavelength of the radiation recorded by the frequency selective photodetectors is set up via the photodetector control block.

I claim:

1. An apparatus for the optical diagnostics of an internal organ of a human body, comprising:

means for positioning at least a portion of the human body;

a source of near infrared electromagnetic radiation interrelated with said positioning means, said near infrared electromagnetic radiation illuminating and being transmitted through said portion of the human body;

means for providing and focusing an amplitude modulated ultrasound beam at said portion of the human body;

a scanning system operably connected to said ultrasound providing and focusing means, said scanning system including means for scanning said amplitude modulated focused ultrasound beam with respect to said source of electromagnetic radiation and said illuminated portion of the human body;

means for detecting said transmitted electromagnetic radiation and recording parameters of amplitude modulation of said electromagnetic radiation with frequency of said amplitude modulated focused ultrasound beam at a near infrared range of wavelengths;

means for synchronizing the scanning of said amplitude modulated focused ultrasound beam with the recording of parameters of said amplitude modulation of said electromagnetic radiation; and means for characterizing a pathological growth found within said portion of the human body upon which said amplitude modulated focused ultrasound beam is directed by monitoring relative changes of said recorded parameters of said amplitude modulation of said electromagnetic radiation based upon the scanning of said amplitude modulated focused ultrasound beam.

2. The apparatus as defined in claim 1 wherein said source of near infrared electromagnetic radiation and said detecting means are both located within said positioning means.

3. The apparatus as defined in claim 1 wherein said source of near infrared electromagnetic radiation provides electromagnetic radiation in the wavelength range of 0.6–1.5 microns.

4. The apparatus as defined in claim 1 wherein said means for providing said amplitude modulated focused ultrasound beam does so at a frequency range of 0.3–10 Mhz.

5. The apparatus as defined in claim 1 wherein said positioning means comprises:

an enclosure made up of a frame closed at one end thereof by a support, the at least a portion of the human body being positioned against said support; and said means for providing said amplitude modulated focused ultrasound beam being located within said enclosure.

6. The apparatus as defined in claim 5 wherein said source of near infrared electromagnetic radiation and said detecting means are both located within one side of said support.

7. The apparatus as defined in claim 5 further comprising:

a member being operably connected to said positioning means for movement with respect thereto, the at least a portion of the human body being located between said member and said positioning means; and said source of near infrared electromagnetic radiation and said detecting means being both located within one side of said support and within one side of said member in opposed relationship to each other.

8. The apparatus as defined in claim 5 wherein said enclosure contains a liquid therein.

9. The apparatus as defined in claim 5 wherein said support is transparent to both near infrared radiation and ultrasound.

10. A method of optical diagnostics of an internal organ of a human body, comprising the steps of:

illuminating at least a portion of a human body with at least one beam of near infrared electromagnetic radiation;

detecting said electromagnetic radiation being transmitted through said portion of a human body;

applying and scanning a focused amplitude modulated ultrasound beam with respect to said portion of a human body being illuminated with said at least one beam of near infrared electromagnetic radiation;

recording parameters of amplitude modulation of said electromagnetic radiation being transmitted through said portion of a human body at a near infrared range of wavelengths;

synchronizing the scanning of said amplitude modulated focused ultrasound beam with the recording of parameters of said amplitude modulation of said electromagnetic radiation; and characterizing a pathological growth found within said portion of the human body upon which said amplitude modulated focused ultrasound beam is directed by monitoring relative changes of said recorded parameters of amplitude modulation of said electromagnetic radiation with frequency of said amplitude modulated focused ultrasound beam based upon the scanning of said amplitude modulated ultrasound beam.

11. The method of optical diagnostics of an internal organ of a human body as defined in claim 10 further comprising the steps of:

employing a pulsed modulation of intensity of said ultrasound beam; and recording the amplitude of modulation of said near infrared radiation appearing as a result of said pulse modulation.

12. The method of optical diagnostics of an internal organ of a human body as defined in claim 11 further comprising the steps of:

varying the cycle of said pulsed modulation; and recording at least one of the parameters of a transient process of intensity modulation of said detected electromagnetic radiation.

13. The method of optical diagnostics of an internal organ of a human body as defined in claim 10 wherein said near infrared electromagnetic radiation is varied in the wavelength range of 0.6–1.5 microns.

14. An apparatus for the optical diagnostics of an internal organ of a human body, comprising:

means for positioning at least a portion of the human body;

a source of near infrared electromagnetic radiation interrelated with said positioning means, said near infrared electromagnetic radiation illuminating and being backscattered from said portion of the human body;

means for providing and focusing an amplitude modulated ultrasound beam at said portion of the human body;

a scanning system operably connected to said ultrasound providing and focusing means said scanning system including means for scanning said amplitude modulated focused ultrasound beam with respect to said source of electromagnetic radiation and said illuminated portion of the human body;

means for detecting said backscattered electromagnetic radiation and recording parameters of amplitude modulation of said electromagnetic radiation with frequency of said amplitude modulated focused ultrasound beam at a near infrared range of wavelengths;

means for synchronizing the scanning of said amplitude modulated focused ultrasound beam with the recording of parameters of said amplitude modulation of said electromagnetic radiation; and means for characterizing a pathological growth found within said portion of the human body upon which said amplitude modulated focused ultrasound beam is directed by monitoring relative changes of said recorded parameters of said amplitude modulation of said electromagnetic radiation based upon the scanning of said amplitude modulated focused ultrasound beam.

15. The apparatus as defined in claim 14 wherein said source of near infrared electromagnetic radiation and said detecting means are both located within said positioning means.

16. The apparatus as defined in claim 14 wherein said source of near infrared electromagnetic radiation provides electromagnetic radiation in the wavelength range of 0.6–1.5 microns.

17. The apparatus as defined in claim 14 wherein said means for providing said amplitude modulated focused ultrasound beam does so at a frequency range of 0.3–10 Mhz.

18. The apparatus as defined in claim 14 wherein said positioning means comprises:
an enclosure made up of a frame closed at one end thereof by a support, the at least a portion of the human body being positioned against said support; and
said means for providing said amplitude modulated focused ultrasound beam being located within said enclosure.

19. The apparatus as defined in claim 18 wherein said source of near infrared electromagnetic radiation and said detecting means are both located within one side of said support.

20. The apparatus as defined in claim 18 further comprising:
a member being operably connected to said positioning means for movement with respect thereto, the at least a portion of the human body being located between said member and said positioning means; and
said source of near infrared electromagnetic radiation and said detecting means being both located within one side of said support and within one side of said member in opposed relationship to each other.

21. The apparatus as defined in claim 18 wherein said enclosure contains a liquid therein.

22. The apparatus as defined in claim 18 wherein said support is transparent to both near infrared radiation and ultrasound.

23. A method of optical diagnostics of an internal organ of a human body, comprising the steps of:
illuminating at least a portion of a human body with at least one beam of near infrared electromagnetic radiation;
detecting said electromagnetic radiation being backscattered from said portion of a human body;
applying and scanning a focused amplitude modulated ultrasound beam with respect to said portion of a human body being illuminated with said at least one beam of near infrared electromagnetic radiation;
recording parameters of amplitude modulation of said electromagnetic radiation being backscattered from said portion of a human body at a near infrared range of wavelengths;
synchronizing the scanning of said amplitude modulated focused ultrasound beam with the recording of parameters of said amplitude modulation of said electromagnetic radiation; and
characterizing a pathological growth found within said portion of the human body upon which said amplitude modulated focused ultrasound beam is directed by monitoring relative changes of said recorded parameters of amplitude modulation of said electromagnetic radiation with frequency of said amplitude modulated focused ultrasound beam based upon the scanning of said amplitude modulated ultrasound beam.

24. The method of optical diagnostics of an internal organ of a human body as defined in claim 23 wherein said near infrared electromagnetic radiation is varied in the wavelength range of 0.6–1.5 microns.

25. The method of optical diagnostics of an internal organ of a human body as defined in claim 23 further comprising the steps of:
employing a pulsed modulation of intensity of said ultrasound beam; and
recording the amplitude of modulation of said near infrared radiation appearing as a result of said pulse modulation.

26. The method of optical diagnostics of an internal organ of a human body as defined in claim 25 further comprising the steps of:
varying the cycle of said pulsed modulation; and
recording at least one of the parameters of a transient process of intensity modulation of said detected electromagnetic radiation.

* * * * *